United States Patent
Pantoja et al.

(10) Patent No.: US 10,100,355 B2
(45) Date of Patent: Oct. 16, 2018

(54) METHODS AND COMPOSITIONS FOR TARGETED NUCLEIC ACID SEQUENCING

(71) Applicant: Illumina, Inc., San Diego, CA (US)

(72) Inventors: Rigo Pantoja, San Diego, CA (US); Marie Hu, Encinitas, CA (US); Erin Bomati, Santee, CA (US); Molly He, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 724 days.

(21) Appl. No.: 14/562,307

(22) Filed: Dec. 5, 2014

(65) Prior Publication Data

US 2015/0159212 A1    Jun. 11, 2015

Related U.S. Application Data

(60) Provisional application No. 61/913,727, filed on Dec. 9, 2013.

(51) Int. Cl.
*C12Q 1/68*    (2018.01)
*C12N 15/10*    (2006.01)
*C12Q 1/6874*    (2018.01)
*C12Q 1/6806*    (2018.01)

(52) U.S. Cl.
CPC ....... *C12Q 1/6874* (2013.01); *C12N 15/1065* (2013.01); *C12N 15/1093* (2013.01); *C12Q 1/6806* (2013.01)

(58) Field of Classification Search
None
See application file for complete search history.

(56) References Cited

U.S. PATENT DOCUMENTS

| | | | | |
|---|---|---|---|---|
| 5,223,414 A * | 6/1993 | Zarling | ................ | C12Q 1/6844 435/6.12 |
| 7,754,429 B2 * | 7/2010 | Rigatti | ................ | C12Q 1/6874 435/6.1 |
| 8,486,625 B2 | 7/2013 | Gunderson et al. | | |
| 2006/0275782 A1 * | 12/2006 | Gunderson | .......... | C12Q 1/6837 435/6.12 |
| 2008/0124810 A1 * | 5/2008 | Terbrueggen | ........ | C12Q 1/6818 436/94 |
| 2010/0120098 A1 * | 5/2010 | Grunenwald | .......... | C12N 15/10 435/91.2 |

FOREIGN PATENT DOCUMENTS

| | | | | |
|---|---|---|---|---|
| WO | WO9300447 | * | 1/1993 | ............... C12Q 1/68 |
| WO | 2012/078312 A2 | | 6/2012 | |
| WO | 2013/117595 | | 8/2013 | |

OTHER PUBLICATIONS

Bentley et al. Accurate whole human genome sequencing using reversible terminator chemistry. Nature. Nov. 6, 2008; 456(7218):53-9.*
Herrmann D, Rose E, Müller U, Wagner R. Microarray-based STR genotyping using RecA-mediated ligation. Nucleic Acids Res. Sep. 2010; 38(17):e172. pp. 1-11. Epub Aug. 3, 2010.*
Sobrino B, Brión M, Carracedo A. SNPs in forensic genetics: a review on SNP typing methodologies. Forensic Sci Int. Nov. 25, 2005; 154(2-3):181-94. Epub Jan. 11, 2005.*
International Search Report for PCT Application No. PCT/US2014/068867, dated Mar. 6, 2015.
Loman, et al., "Performance comparison of benchtop high-throughput sequencing platforms", Nature Biotechnology, 30, 2012, 434-439.
Rabbani, et al., "Next-generation sequencing: impact of exome sequencing in characterizing Mendelian disorders", Journal of Human Genetics, 57, 2012, 621-632.
Rothberg, et al., "An integrated semiconductor device enabling non-optical genome sequencing", Nature, 475, 2011, 348-352.
Zhumabayeva, et al., "RecA-Mediated Affinity Capture: A Method for Full-Length cDNA Cloning", Biotechniques, 27, 1999, 834-845.

* cited by examiner

*Primary Examiner* — Samuel C Woolwine
*Assistant Examiner* — Olayinka A Oyeyemi
(74) *Attorney, Agent, or Firm* — Illumina, Inc.

(57) ABSTRACT

Embodiments provided herein relate to methods and compositions for obtaining nucleic acid sequence information. Some embodiments provided herein include methods and compositions for preparing nucleic acid libraries. In some embodiments, such nucleic acid libraries are useful for targeted nucleic acid sequencing.

23 Claims, 5 Drawing Sheets

METHODS AND COMPOSITIONS FOR TARGETED NUCLEIC ACID SEQUENCING

FIELD OF THE INVENTION

Embodiments provided herein relate to methods and compositions for obtaining nucleic acid sequence information. Some embodiments provided herein include methods and compositions for preparing nucleic acid libraries. In some embodiments, such nucleic acid libraries are useful for targeted nucleic acid sequencing.

BACKGROUND OF THE INVENTION

Through massive parallelization and miniaturization, the throughput of DNA sequencing has been increased tremendously while the cost of sequencing has been reduced by several orders of magnitude compared to the conventional gel or capillary-based sequencers using the Sanger dideoxy sequencing method. Targeted gene sequencing has proven its utility in the clinical space. For example, more than 102 Mendelian disorders have been identified using targeted sequencing (Rabbani B. et al., 2012, J. Hum. Genet. 57:621-632). The advantages of targeted sequencing include fast turnaround, simplified ethical considerations with unintended findings, greater depth coverage, and significantly decreased throughput. Preparation of nucleic acid libraries for targeted sequencing often includes multiple steps that may take several days to complete. Despite recent progress and developments, further improvements are still needed.

SUMMARY OF THE INVENTION

Some embodiments of the methods and compositions provided herein include a method for preparing a targeted nucleic acid library comprising: (a) providing a nucleic acid library comprising a plurality of different nucleic acids and a double-stranded target nucleic acid; (b) hybridizing a first adapter probe with the target nucleic acid in the presence of a recombinase, wherein the first adapter probe comprises a first portion complementary to a substrate probe and a second portion exogenous to the first portion and complementary to at least a portion of the double-stranded target nucleic acid, and wherein the recombinase promotes hybridizing the second portion with the double-stranded target nucleic acid; (c) extending the hybridized first adapter probe; (d) hybridizing the extended adapter probe with the substrate probe, wherein the substrate probe is immobilized on a first substrate; and (e) extending the hybridized substrate probe to form an anchor probe, thereby obtaining a targeted nucleic acid library.

Some embodiments also include: (f) hybridizing a second adapter probe comprising a first portion complementary to a capture probe and a second portion exogenous to the first portion and complementary to at least a portion of the anchor probe with the anchor probe; (g) extending the hybridized anchor probe; (h) hybridizing the extended anchor probe with the capture probe, wherein the capture probe is immobilized on a second substrate; and (i) extending the capture probe to form a modified capture probe.

In some embodiments, (c) comprises polymerase extension. In some embodiments, the polymerase extension comprises a polymerase chain reaction.

In some embodiments, (e) comprises polymerase extension.

In some embodiments, (e) comprises ligation of a nucleic acid complementary to the extended adapter probe with the substrate probe.

In some embodiments, the first adapter probe comprises a sequence selected from the group consisting of a locus-specific sequence and an allele-specific sequence.

In some embodiments, the second adapter probe comprises a sequence selected from the group consisting of a locus-specific sequence and an allele-specific sequence.

In some embodiments, the double-stranded target nucleic acid comprises genomic DNA.

In some embodiments, the recombinase comprises RecA.

In some embodiments, the first substrate comprises a bead.

In some embodiments, the bead is associated with an individual site of a substrate.

In some embodiments, the site is configured to have a single associated bead.

In some embodiments, the first and the second substrate are the same.

In some embodiments, the nucleic acid library is prepared by contacting a nucleic acid with a transposon.

In some embodiments, the nucleic acid library comprises a plurality of sequences selected from mosaic elements, indices, and sequencing adapters.

In some embodiments, the nucleic acid library is produced by tagging and fragmenting activities of a transposase.

Some embodiments of the methods and compositions provided herein include a method of detecting a plurality of nucleic acid sequences comprising: obtaining a nucleic acid library prepared according to any one of the foregoing methods; and detecting the modified capture probes, thereby detecting the plurality of target nucleic acid sequences.

Some embodiments of the methods and compositions provided herein include a nucleic acid library prepared according to any one of the foregoing methods.

Some embodiments of the methods and compositions provided herein include a flow cell comprising the foregoing nucleic acid library.

Some embodiments of the methods and compositions provided herein include a method of preparing a nucleic acid library comprising: (a) providing a plurality of anchor probes; (b) hybridizing a plurality of double-stranded target nucleic acids with the plurality of anchor probes in the presence of a recombinase under conditions wherein the recombinase promotes the hybridizing with the target nucleic acids; (c) hybridizing the plurality of double-stranded target nucleic acids with a plurality of ligation probes in the presence of a recombinase under conditions wherein the recombinase promotes the hybridizing with the target nucleic acids; (d) extending the anchor probes or the ligation probes; and (e) ligating the anchor probes to the ligation probes to form a plurality of different extended ligated probes, thereby preparing the library of nucleic acids.

In some embodiments, (d) comprises extending the anchor probes to form extended anchor probes and (e) comprises ligating the extended anchor probes to the ligation probes to form the plurality of different extended ligated probes, thereby preparing the library of nucleic acids.

In some embodiments, (d) comprises extending the ligation probes to form extended ligation probes and (e) comprises ligating the extended ligation probes to the anchor probes to form the plurality of different extended ligated probes, thereby preparing the library of nucleic acids.

In some embodiments, the anchor probes are prepared by a method comprising: (i) providing one or more first substrates comprising a plurality of substrate probes immobilized thereon; (ii) providing a plurality of different adapter nucleic acids, each adapter nucleic acid comprising a first portion complementary to a substrate probe and a second portion exogenous to the first portion and complementary to at least a portion of a double-stranded target nucleic acid; (iii) hybridizing the substrate probes with the first portions of the adapter nucleic acids; and (iv) extending the substrate probes to form anchor probes comprising the complement of the second portion of the adapter nucleic acid.

Some embodiments also include: (f) providing one or more second substrates comprising a plurality of capture probes immobilized thereon; (g) hybridizing each ligation probe to a capture probe; and (h) modifying the capture probes by polymerase extension.

Some embodiments also include: amplifying the library of nucleic acids comprising: hybridizing a plurality of amplifier probes with the anchor probes and ligation probes; and amplifying the extended ligated probes.

In some embodiments, the amplifying comprises a polymerase chain reaction.

In some embodiments, extending the substrate probes comprises polymerase extension.

In some embodiments, (b) is after (c). In some embodiments, nonhybridized target nucleic acids are removed after (c) and before (b).

In some embodiments, wherein (b) is before (c). In some embodiments, nonhybridized target nucleic acids are removed after (b) and before (c).

In some embodiments, at least a portion of the substrate probes are the same.

In some embodiments, at least a portion of the capture probes are the same.

In some embodiments, each anchor probe comprises a sequence selected from the group consisting of a locus-specific sequence and an allele-specific sequence.

In some embodiments, each ligation probe comprises a sequence selected from the group consisting of a locus-specific sequence and an allele-specific sequence.

In some embodiments, each anchor probe comprises a locus-specific sequence and each ligation probe comprises an allele-specific sequence.

In some embodiments, the double-stranded target nucleic acids comprise genomic DNA.

In some embodiments, the recombinase comprises RecA.

In some embodiments, the plurality of anchor probes are associated with individual sites of a substrate.

In some embodiments, the plurality of capture probes are associated with individual sites of a substrate.

In some embodiments, the plurality of substrate probes are associated with individual sites of a substrate.

In some embodiments, the first substrates comprises a plurality of beads.

In some embodiments, the beads are associated with individual sites of a substrate.

In some embodiments, each of the sites is configured to have a single associated bead.

In some embodiments, at least a portion of the first and the second substrates are the same substrates.

In some embodiments, the plurality of anchor probes comprises an array on a substrate.

In some embodiments, the array is made by a method selected from the group consisting of a spotting technique, photolithographic technique, and printing technique.

Some embodiments of the methods and compositions provided herein include a method of detecting a plurality of nucleic acid sequences comprising: obtaining a nucleic acid library prepared according to any one of the foregoing methods; and detecting the modified capture probes, thereby detecting the plurality of target nucleic acid sequences.

Some embodiments of the methods and compositions provided herein include a nucleic acid library prepared according to any one of the foregoing methods.

Some embodiments of the methods and compositions provided herein include a flow cell comprising the foregoing nucleic acid library.

Some embodiments of the methods and compositions provided herein include a method of detecting a nucleic acid comprising: (a) providing an anchor probe; (b) hybridizing a double-stranded target nucleic acid with the anchor probe in the presence of a recombinase under conditions wherein the recombinase promotes the hybridizing with the target nucleic acid; (c) hybridizing the double-stranded target nucleic acid with a ligation probe in the presence of a recombinase under conditions wherein the recombinase promotes the hybridizing with the target nucleic acid; (d) extending the anchor probe or the ligation probe; (e) ligating the anchor probe to the ligation probe to form an extended ligated probe; and (f) detecting the extended ligated probe, thereby detecting the nucleic acid.

In some embodiments, the anchor probe is prepared by a method comprising: (i) providing a first substrate comprising a substrate probe immobilized thereon; (ii) providing an adapter nucleic acid comprising a first portion complementary to a substrate probe and a second portion exogenous to the first portion and complementary to at least a portion of a double-stranded target nucleic acid; (iii) hybridizing the substrate probe with the first portion of the adapter nucleic acid; and (iv) extending the substrate probe to form the anchor probe comprising the complement of the second portion of the adapter nucleic acid.

Some embodiments also include: (g) providing a second substrate comprising a capture probe immobilized thereon; (h) hybridizing the ligation probe to a capture probe; and (i) modifying the capture probe by polymerase extension.

Some embodiments also include amplifying the extended ligated probe comprising: hybridizing a plurality of amplifier probes with the anchor probes and ligation probes; and amplifying the extended ligated probe.

In some embodiments, the amplifying comprises a polymerase chain reaction.

In some embodiments, extending the substrate probe comprises polymerase extension.

In some embodiments, (b) is after (c).

In some embodiments, the anchor probe comprises a sequence selected from the group consisting of a locus-specific sequence and an allele-specific sequence.

In some embodiments, the ligation probe comprises a sequence selected from the group consisting of a locus-specific sequence and an allele-specific sequence.

In some embodiments, the anchor probe comprises a locus-specific sequence and the capture probe comprises an allele-specific sequence.

In some embodiments, the double-stranded target nucleic acid comprises genomic DNA.

In some embodiments, the recombinase comprises RecA.

In some embodiments, the first substrate comprises a bead.

In some embodiments, the bead is associated with an individual site of a substrate.

In some embodiments, the site is configured to have a single associated bead.

In some embodiments, the first and the second substrate are the same.

Some embodiments of the methods and compositions provided herein include a method of preparing a nucleic acid library: (a) preparing a plurality of anchor probes; (b) providing a plurality of second adapter nucleic acids, each comprising a first portion and a second portion exogenous to the first portion; (c) hybridizing the first portion of the second adapter nucleic acids with the anchor probes; (d) extending the anchor probes with sequences complementary to at least a portion of the second portion of the second adapter nucleic acids; (h) hybridizing the extended anchor probes with the capture probes; and (i) modifying the capture probes by polymerase extension.

In some embodiments, preparing a plurality of anchor probes comprises: (i) providing one or more substrates comprising a plurality of substrate probes and a plurality of capture probes immobilized thereon; (ii) providing a plurality of different first adapter nucleic acids, each comprising a first portion and a second portion exogenous to the first portion; (iii) hybridizing the first portion of the first adapter nucleic acids with the substrate probes; and (iv) extending the substrate probes, thereby preparing the anchor probes.

In some embodiments, extending the substrate probes comprises ligating target nucleic acid to the substrate probes.

In some embodiments, the target nucleic acids comprise single-stranded nucleic acids.

In some embodiments, the target nucleic acids comprise genomic DNA.

In some embodiments, extending the anchor probes comprises polymerase extension.

In some embodiments, modifying the capture probes comprises a polymerase chain reaction.

In some embodiments, the one or more substrates comprises a plurality of beads.

Some embodiments of the methods and compositions provided herein include a method of preparing a nucleic acid library: (a) preparing an anchor probe; (b) providing a second adapter nucleic acid comprising a first portion and a second portion exogenous to the first portion; (c) hybridizing the first portion of the second adapter nucleic acid with the anchor probe; (d) extending the anchor probe with sequences complementary to at least a portion of the second portion of the second adapter nucleic acid; (h) hybridizing the extended anchor probe with the capture probe; and (i) modifying the capture probe by polymerase extension.

In some embodiments, preparing the anchor probe comprises: (i) providing a substrate comprising a substrate probe and a capture probe immobilized thereon; (ii) providing a first adapter nucleic acid comprising a first portion and a second portion exogenous to the first portion; (iii) hybridizing the first portion of the first adapter nucleic acid with the substrate probe; and (iv) extending the substrate probe, thereby preparing the anchor probe.

In some embodiments, extending the substrate probe comprises ligating a target nucleic acid to the substrate probe.

In some embodiments, the target nucleic acid comprises a single-stranded nucleic acid.

In some embodiments, the target nucleic acid comprises genomic DNA.

In some embodiments, extending the anchor probe comprises polymerase extension.

In some embodiments, modifying the capture probe comprises a polymerase chain reaction.

In some embodiments, the substrate comprises a bead.

In some embodiments, the bead is associated with an individual site of a substrate.

In some embodiments, the site is configured to have a single associated bead.

DETAILED DESCRIPTION

Figure 1:
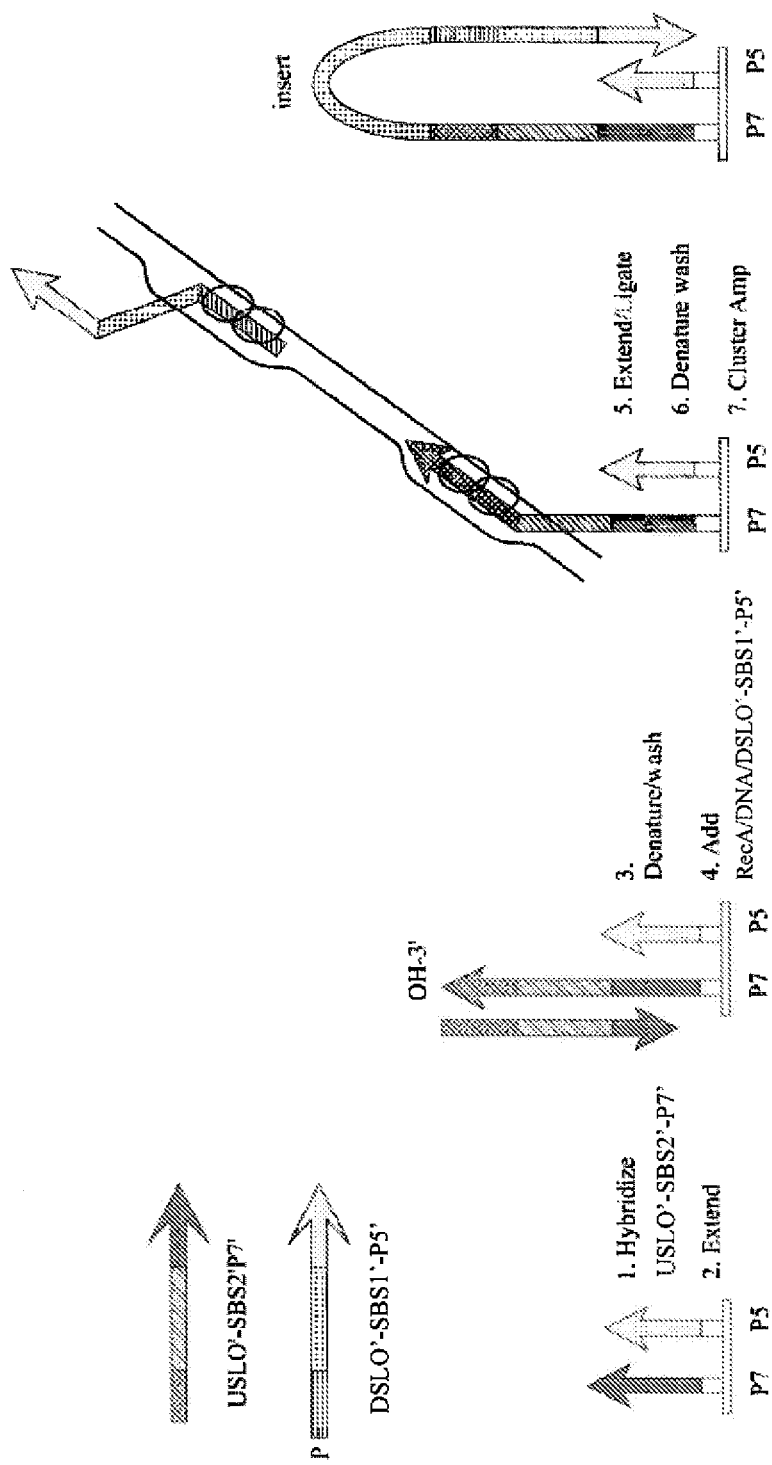
FIG. 1 depicts an embodiment of a method for adapting a universal biochip to capture certain target nucleic acids, and efficient recombinase-promoted hybridization of probes with a double-stranded target nucleic acid, and preparation of a substrate for cluster amplification on the biochip.

Embodiments provided herein relate to methods and compositions for obtaining nucleic acid sequence information. Some embodiments provided herein include methods and compositions for preparing nucleic acid libraries. In some embodiments, such nucleic acid libraries are useful for targeted nucleic acid sequencing.

Embodiments of the methods and compositions provided herein include the use of recombinases in the preparation of targeted nucleic acid libraries. Typically, target nucleic acid libraries can be prepared over several days in a series of steps that include hybridizing double-stranded target nucleic acids in a nucleic acid library with specific probes. Such hybridized probes can be used to amplify target sequences and prepare a targeted nucleic acid library. Advantageously, the methods and compositions provided herein include the use of recombinases which increase the efficiencies of certain hybridization steps, reducing the need for amplification of target nucleic acid sequences, and reducing the time taken to prepare a targeted nucleic acid library. In addition, the methods and compositions provided herein include the preparation of targeted nucleic acid libraries using universal biochip substrate (e.g. universal nucleic acid arrays).

Some embodiments of the methods and compositions provided herein include preparing nucleic acid libraries useful for targeted nucleic acid sequencing including: hybridization of an adapter nucleic acid comprising an upstream target sequence with an anchor probe; extension of the anchor probe to incorporate the complement of the upstream target sequence; hybridization of a double-stranded target nucleic acid with the anchor probe, and with a ligation probe comprising a downstream target sequence under conditions in which a recombinase promotes the hybridization; extension of the anchored probe or the ligation probe; ligation of the anchor probe and ligation probe to form an extended ligated probe; and bridge cluster amplification of the extended ligated probe.

Advantageously, some of the methods and compositions provided herein can include the use of universal biochips with preparation of a nucleic acid at high efficiencies. In some embodiments, a universal biochip can comprises a population of substrate probes comprising universal nucleic acid sequences and a population of capture probes comprising universal nucleic acid sequences. For example, in some embodiments, the population of substrate probes and the population of capture probes can comprise P7 and P5 sequences, respectively. P7 and P5 sequences are useful universal sequences as described, for example, in U.S. Pat. No. 8,563,477, which is incorporated herein by reference. The universal biochip can be adapted to capture particular target sequences by extending the substrate probes to include sequences that are complementary to desired target sequences, thereby forming target-specific anchor probes. In some such embodiments, an adapter nucleic acid is hybridized to the substrate probe, and the substrate probe is extended with sequences complementary to the adapter nucleic acid. The adapter nucleic acid can include sequences of certain target nucleic acids. Thus, a universal biochip can be adapted to capture particular target sequences.

In addition, some of the methods and compositions provided herein can include the use of a biochip to capture particular target sequences at high efficiencies. In some embodiments, double-stranded target nucleic acids are hybridized to target-specific anchor probes and target-specific ligation probes under conditions in which a recombinase promotes hybridization of the probes with the double-stranded target nucleic acid. Such increased efficiencies of capturing particular target sequences reduce the amount of nucleic acids that need to be used in preparing a nucleic acid library. In addition, such increased efficiencies reduce the need for amplifying a sample comprising a target nucleic acid before contacting the sample with the biochip. Eliminating the step of amplifying a sample comprising a target nucleic acid also reduces bias that may arise due to amplification of a sample. Thus, some of the methods and compositions provided herein can include simultaneous library preparation and flow cell annealing. In some embodiments, manual library preparation is obviated by automation, thus minimizing the handling of samples comprising target nucleic acids. Moreover, the use of a recombinase, such as RecA can efficiently promote sequence specificity and sensitivity.

As used herein, "at least a portion" can include at least about 1%, about 5%, about 10%, about 20%, about 30%, about 40%, about 50%, about 60%, about 70%, about 80%, about 90%, about 95%, about 99%, and about 100% of a whole.

As used herein, "nucleic acid" can include at least two nucleotides covalently linked together. A nucleic acid generally includes phosphodiester bonds, although in some embodiments, nucleic acid analogs may have alternate backbones, for example, phosphoramide, phosphorothioate, phosphorodithioate, O-methylphosphoroamidite linkages (Eckstein, Oligonucleotides and Analogues: A Practical Approach, Oxford University Press), and peptide nucleic acid backbones and linkages (Egholm, J. Am. Chem. Soc. 114:1895 (1992); Meier et al., Chem. Int. Ed. Engl. 31:1008 (1992); Nielsen, Nature 365:566 (1993); Carlsson et al., Nature 380:207 (1996), all of which are incorporated by reference). Other analog nucleic acids include those with positive backbones; non-ionic backbones and non-ribose backbones. Nucleic acids containing one or more carbocyclic sugars are also included within the definition of nucleic acids (Jenkins et al., Chem. Soc. Rev. (1995) pp 169-176, which is incorporated by reference). Several nucleic acid analogs are described in Rawls, C & E News Jun. 2, 1997, page 35, which is incorporated by reference. These modifications of the ribose-phosphate backbone may be done to facilitate the addition of labels, or to increase the stability and half-life of such molecules in physiological environments. Nucleic acids may be single-stranded or double-stranded, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. Some embodiments may utilize isocytosine and isoguanine.

Some embodiments of the methods and compositions provided herein include target nucleic acids. As used herein "target nucleic acid" can include any nucleic acid of interest or nucleic acid sequence of interest. Examples of some sources of target nucleic acids can include at least a portion of a gene; regulatory sequence; genomic DNA; cDNA; circular DNA; low molecular weight DNA, plasmid DNA; circulating DNA, circulating tumor DNA (ctDNA); hnRNA; mRNA; noncoding RNA including rRNA, tRNA, micro RNA, small interfering RNA, small nucleolar RNA, small nuclear RNA and small temporal RNA; fragmented or degraded nucleic acids; methylated nucleic acids; PNAs; nucleic acid obtained from subcellular organelles such as mitochondria or chloroplasts; and nucleic acids obtained from microorganisms, parasites, or DNA or RNA viruses that may be present in a biological sample. Sources of target nucleic acids can include also include synthetic nucleic acid sequences that may or may not include nucleotide analogs that are added or spiked into a biological sample. Target nucleic acids can be amplicons produced from the sources exemplified above or otherwise known in the art.

In some embodiments, target nucleic acids may be obtained or further processed by a variety of methods. Some embodiments include shearing a source of a target nucleic acid, example methods include sonicating, acoustic shearing, nebulizing, needle shearing, and enzymatic fragmenting. In some embodiments, certain sequences of a source may be amplified. In some embodiments, a source may be fragmented and indexed. Example methods of fragmenting and indexing source nucleic acids to prepare target nucleic acids useful with the methods and compositions described herein are described in U.S. Pub. No. 2011/0246084, and U.S. Pub. No. 2012/0122737, each of which is expressly incorporated herein by reference in its entirety. Other methods that can be used to fragment and index nucleic acids are described, for example, in U.S. Pat. No. 6,107,023; U.S. Pat. No. 5,641,658; US 2002/0055100; U.S. Pat. No. 7,115,400; US 2004/0096853; US 2004/0002090; US 2007/0128624; and US 2008/0009420, each of which is incorporated herein by reference.

Some embodiments of the methods and compositions provided herein include the use of probes. As used herein, "probe" can include a nucleic acid, such as a primer or an oligonucleotide that can hybridize to at least a portion of a particular nucleic acid. In some embodiments, probes are designed to be complementary to at least a portion of a particular nucleic acid such that selective hybridization of the probe and particular nucleic acid can occur. In some embodiments, the complementarity need not be perfect;

there may be any number of base pair mismatches which will interfere with hybridization between the probe and particular nucleic acid. Another example of a useful probe is a nucleic acid that functions as a primer for nucleotide extension or oligonucleotide ligation.

If the number of mismatches is so great that no hybridization can occur under even the least stringent of hybridization conditions, a probe is not a complementary to a particular nucleic acid. As used herein, "substantially complementary" can include a probe that is sufficiently complementary to a particular nucleic acid to hybridize under normal reaction conditions. A variety of hybridization conditions may be used with the compositions and methods provided herein, including high, moderate and low stringency conditions; see for example Maniatis et al., Molecular Cloning: A Laboratory Manual, 2d Edition, 1989, hereby incorporated by reference in its entirety. Thus, methods set forth herein can generally be run under stringency conditions which allow formation of the hybridization complex only in the presence of the particular nucleic acid. Stringency can be controlled by altering a step parameter that is a thermodynamic variable, including, but not limited to, temperature, formamide concentration, salt concentration, chaotropic salt concentration, pH, organic solvent concentration, etc. In some embodiments, hybridization between a probe and target nucleic acid may be further promoted using an enzyme, such as a recombinase.

Methods of Preparing Nucleic Acid Libraries and Enriching Target Nucleic Acids

Some of the methods and embodiments provided herein include preparing a targeted nucleic acid library. In some embodiments, a targeted nucleic acid library may be prepared from a substrate nucleic acid library such that the targeted nucleic acid is enriched in certain target nucleic acids. In some embodiments, a substrate nucleic acid can include any a substrate nucleic acid prepared by contacting a nucleic acid with a transposon. In some embodiments, a substrate nucleic acid can include sequencing adapters, for example adapter sequences useful in nucleic acid sequencing methods; indices, for example index sequences useful in assembling sequence information from a plurality of fragments into a contiguous fragment; and inserted transposon sequences such as mosaic elements. In some embodiments, a substrate nucleic acid library can include a library prepared by the methods described in U.S. Pub No. 20120208705, which is incorporated herein by reference in its entirety. In some embodiments, a substrate nucleic acid library can include a NEXTERA nucleic acid library (commercially available from Illumina, Inc., San Diego).

Some of the methods and compositions provided herein include methods of preparing a nucleic acid library, such as a targeted nucleic acid library. In some embodiments, a plurality of anchor probes is obtained or provided. The plurality of anchor probes can be prepared by methods that include providing one or more first substrates comprising a plurality of substrate probes immobilized on the one or more substrates. In some embodiments, one or more substrate probes can be different (i.e. having different nucleotide sequences from each other). In particular embodiments, the number of different probes can be at least 100, $1\times10^3$, $1\times10^4$, $1\times10^5$, $1\times10^6$, $1\times10^7$, $1\times10^8$, or more. Alternatively or additionally, the number of different probes can be at most $1\times10^8$, $1\times10^7$, $1\times10^6$, $1\times10^5$, $1\times10^4$, $1\times10^3$, 100 or less. In some embodiments, the substrate probes can comprise or consist of the same sequences. In some embodiments, a substrate probe sequence can include a universal primer, such as the P7 sequence. In some embodiments, the substrate probe is extended to form an anchor probe.

Anchor probes can be prepared by extending a substrate probe. In some embodiments, a substrate probe is extended by hybridizing an adapter nucleic acid with a substrate probe, and extending the substrate probe by polymerase extension. In some embodiments, an adapter nucleic acid includes a first portion with a sequence complementary to the substrate probe, and a second portion exogenous to the first portion. The second portion of the adapter nucleic acid can include at least a portion of a target nucleic acid sequence. In some embodiments, the adapter nucleic acid can also include complements of a sequencing primer, an index, and other sequences useful for an individual component in a nucleic acid library. Thus, the anchor probe can include a contiguous sequence including a substrate probe and a sequence that is complementary to at least a portion of a target nucleic acid sequence, and may also include a sequencing primer sequence, index, or other sequence(s) useful for an individual component in a nucleic acid library.

Some of the methods and compositions provided herein include ligation probes. A ligation probe can include a first portion comprises a sequence complementary to at least a portion of a target nucleic acid, and a second portion exogenous to the first portion. The second portion of the ligation probe can include sequences complementary to a capture probe. In some embodiments, the ligation probe can also include a sequencing primer sequence, an index, or other sequence(s) useful for an individual component in a nucleic acid library.

In some embodiments, a target nucleic acid is selectively hybridized with a ligation probe. In some embodiments, the hybridizing can be under conditions in which a recombinase promotes the hybridizing of the target nucleic acid with the ligation probe. In some embodiments, a target nucleic acid is selectively hybridized with an anchor probe. In some embodiments, the hybridizing can be under conditions in which a recombinase promotes the hybridizing of the target nucleic acid with the anchor probe. In some such embodiments, the target nucleic acid is double-stranded. In some embodiments, the target nucleic acid is double-stranded. In some embodiments, hybridizing the target nucleic acid with the anchor probe can be before, after, or at the same time as hybridizing the target nucleic acid with the ligation probe.

Examples of useful recombinases include, but are not limited to, RecA, T4 UvsX protein, any homologous protein or protein complex from any phyla, or functional variants thereof. Eukaryotic RecA homologues are generally named Rad51 after the first member of this group to be identified. Other non-homologous recombinases may be utilized in place of RecA, for example, RecT or RecO. Useful components of recombinase-facilitated extension and reaction conditions are set forth in U.S. Pat. No. 5,223,414 and U.S. Pat. No. 7,399,590, each of which is incorporated herein by reference.

In some embodiments, the anchor probe and ligation probe each hybridize to the same strand of a target nucleic acid. In some embodiments, the anchor probe and ligation probe hybridize to either end of a sequence of interest in the target nucleic acid. For example, the anchor probe can hybridize with a sequence upstream of a sequence of interest, and the ligation probe can hybridize with a sequence downstream of a sequence of interest; or the anchor probe can hybridize with a sequence downstream of a sequence of interest, and the ligation probe can hybridize with a sequence upstream of a sequence of interest.

In some embodiments, the anchor probe comprises a sequence selected from the group consisting of a locus-specific sequence and an allele-specific sequence. In some embodiments, the ligation probe comprises a sequence selected from the group consisting of a locus-specific sequence and an allele-specific sequence. In some embodiments, the anchor probe comprises a locus-specific sequence and the ligation probe comprises an allele-specific sequence. A locus specific sequence is one that is identical to or complementary to a portion of a genetic locus that is not expected to include polymorphisms. An allele-specific sequence is one that is identical to or complementary to a portion of a genetic locus that is expected to include polymorphisms. Thus, an allele-specific sequence can distinguish one allele at a locus from at least one other allele at that locus. The alleles can be, for example, sequence portions that differ from each other due to single nucleotide polymorphisms, sequence insertions, or deletions of sequences.

In some embodiments either the anchor probe or the ligation probe is extended. The extended sequence can be complementary to the sequence of interest. The extension can be by polymerase extension or ligase extension. In some embodiments, the extended anchor probe is ligated to the ligation probe to form an extended ligated probe; or the extended ligation probe is ligated to the anchor probe to form an extended ligated probe. As will be understood, each extended product can comprise sequences of a substrate probe, a sequence complementary to a target nucleic acid, and a ligation probe. Examples of ligation methods useful with the methods and compositions provided herein are described in U.S. Pat. No. 8,486,625, which is incorporated by reference herein in its entirety. In some embodiments, methods such as the oligonucleotide ligation assay may be used (OLA). OLA involves the ligation of at least two smaller probes into a single long probe, using the target sequence as the template for the ligase. See generally U.S. Pat. Nos. 5,185,243, 5,679,524 and 5,573,907; EP 0 320 308 B1; EP 0 336 731 B1; EP 0 439 182 B1; WO 90/01069; WO 89112696; and WO 89/09835, all of which are incorporated by reference. Two, three or more probes can be ligated to form an extended ligated probe in a method set forth herein. For example, a ligation probe and an anchor probe can be ligated to opposite ends of an intermediate probe to form a ternary probe (e.g. 5'-ligation probe-intermediate probe-anchor probe-3' or 5'-anchor probe-intermediate probe-ligation probe-3'). The probes may or may not be extended by polymerase catalyzed addition of one or more nucleotide prior to ligation.

In some embodiments, the extended ligated probe can be amplified by cluster amplification. Examples of cluster amplification useful with the methods and compositions provided herein are described in U.S. Pub. No. 2012/0122737, which is incorporated by reference herein in its entirety. In some such embodiments, at least a portion of the extended ligated probe is hybridized with a capture probe. In some embodiments, the capture probe is immobilized on one or more substrates. In some embodiments, one or more capture probes can be different. In some embodiments, the capture probes can comprise or consist of the same sequence. In some embodiments, a capture probe can include the sequence of a universal primer, for example, the P5 sequence. In some embodiments, the capture probe can be extended by polymerase extension with a sequence complementary to the extended ligated probe. In some embodiments, the polymerase extension is a polymerase chain reaction.

In other embodiments, the extended ligated probe can be amplified in solution. In some embodiments, amplifier probes are hybridized with the extended ligated probe, and the amplifier probes extended by polymerase extension. In some embodiments, the polymerase extension is a polymerase chain reaction.

More methods and compositions provided herein include methods for preparing a targeted nucleic acid library. In some embodiments, an adapter probe is hybridized to a target nucleic acid. In some embodiments, the adapter probe is hybridized to a double-stranded target nucleic acid under conditions in the presence of a recombinase wherein the recombinase promotes the hybridizing with the double-stranded target nucleic acid. In some embodiments, the target nucleic acid is in a nucleic acid library. In some embodiments, the hybridized adapter probe is extended by polymerase extension to generate an extended adapter probe comprising a complement to the target nucleic acid. In some embodiments, the extended adapter probe comprising the complement to the target nucleic acid is amplified, for example, by a polymerase chain reaction. Advantageously, the increase in efficiency with the use a recombinase means that in some embodiments of the methods provided herein, amplification of target nucleic acids is not needed prior to and/or after formation of an extended ligated probe.

In some embodiments, the extended adapter probe comprising the complement to the target nucleic acid is associated with a substrate. In some embodiments, the extended adapter probe is hybridized to a substrate probe immobilized on a substrate. The substrate probe is extended with sequences complementary to the extended adapter probe. In some embodiments, the extension is a polymerase extension. In some embodiments, the extension is a ligation reaction between a nucleic acid having sequences complementary to the extended adapter probe and with the substrate probe. The extended substrate probe forms an anchor probe comprising target nucleic acids.

In some embodiments, an anchor probe can be amplified by further extending the anchor probe with sequences complementary to a capture probe. In some embodiments, an adapter probe with sequences complementary to the anchor probe comprising the target nucleic acids and the capture probe is hybridized to the anchor probe. In some embodiments, the anchor probe is extended by polymerase extension with sequences complementary to the adapter probe and the capture probe. The extended anchor probe is hybridized to the capture probe. In some embodiments, the hybridized capture probe can be extended by polymerase extension. In some embodiments, the polymerase extension is a polymerase chain reaction. Examples of such extensions include cluster amplification reactions on a substrate as further provided herein.

A method set forth herein can use any of a variety of amplification techniques. Exemplary techniques that can be used to amplify nucleic acid species set forth herein include, but are not limited to, polymerase chain reaction (PCR), rolling circle amplification (RCA), multiple displacement amplification (MDA), or random prime amplification (RPA). For example, one or more primers used for amplification can be attached to a solid phase at the amplification site. In PCR embodiments, one or both of the primers used for amplification can be attached to a solid phase. Formats that utilize two species of primer attached to the surface are often referred to as bridge amplification because double stranded amplicons form a bridge-like structure between the two surface-attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference.

Solid-phase PCR amplification can also be used to amplify nucleic acid species set forth herein. In such embodiments, one of the amplification primers can be attached to a solid support and the second primer can be in solution. An exemplary format that uses a combination of a surface attached primer and soluble primer is emulsion PCR as described, for example, in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional. The above-exemplified PCR techniques can be modified for non-cyclic amplification (e.g. isothermal amplification) using components exemplified elsewhere herein for facilitating or increasing the rate of amplification.

RCA techniques can be used to amplify nucleic acid species set forth herein. Exemplary components that can be used in an RCA reaction and principles by which RCA produces amplicons are described, for example, in Lizardi et al., *Nat. Genet.* 19:225-232 (1998) and US 2007/0099208 A1, each of which is incorporated herein by reference. Primers used for RCA can be in solution or attached to a solid support surface at an amplification site.

MDA techniques can be used to amplify nucleic acid species set forth herein. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); U.S. Pat. No. 5,455,166; U.S. Pat. No. 5,130,238; and U.S. Pat. No. 6,214,587, each of which is incorporated herein by reference. Primers used for MDA can be in solution or attached to a solid support surface.

Some of the methods and compositions provided herein include methods of preparing a nucleic acid library that include ligating a target nucleic acid with a substrate probe, extending the ligated target nucleic acid by polymerase extension and amplifying the extended ligated probe by cluster amplification.

In some embodiments, ligating a target nucleic acid with a substrate probe includes hybridizing an adapter nucleic acid to a substrate probe. The adapter nucleic acid can include a first portion comprising sequences that hybridizes to the substrate probe, and a second portion exogenous to the first portion comprising sequences that hybridize to the target nucleic acid. The second portion of the adapter nucleic acid hybridizes to the target nucleic acid such that the target nucleic acid can be ligated to the substrate probe to form a ligated target nucleic acid.

In some embodiments, the target nucleic acid can be extended prior to ligation with the substrate probe, or subsequent to ligation with the substrate probe. In some embodiments, the target nucleic acid can be extended by hybridizing a second adapter nucleic acid with the target nucleic acid. The second adapter nucleic acid can include a first portion comprising sequences that hybridize to the target nucleic acid, and a second portion comprising sequences that hybridize to a capture probe. Subsequent to hybridization of the second adapter nucleic acid to the target nucleic acid, the target nucleic acid can be extended by polymerase extension. In some embodiments, an extended ligated target nucleic acid can be formed that includes a substrate probe, target nucleic acid sequences, and sequences complementary to the second adapter nucleic acid.

In some embodiments, the extended ligated target nucleic acid can be amplified. In some embodiments, the amplification is cluster amplification in which the extended ligated target nucleic acid is hybridized with a capture probe, and the capture probe is extended by polymerase extension. In some embodiments, the polymerase extension is polymerase chain extension. In some embodiments sequences complementary to the second adapter nucleic acid of the extended ligated target nucleic acid hybridize with the capture probe.

Substrates

Some of the methods and compositions provided herein include a nucleic acid immobilized on a substrate. In some embodiments, the nucleic acid can include a nucleic acid provided herein, for example, a substrate probe, an anchor probe, a capture probe, extended ligated anchor probes, and extended ligated target nucleic acids. The various nucleic acids provided herein can be immobilized on the same or different substrates. For example, in some embodiments, an anchor probe and a capture probe are immobilized on the same substrate. In some embodiments, an anchor probe and a capture probe are immobilized on different substrates.

In some embodiments, nucleic acids provided herein are distributed on a planar surface. In some embodiments, the nucleic acids are distributed at discrete sites on the planar surface. In some embodiments, the discrete sites are wells. In some embodiments, the nucleic acids are immobilized on a substrate, such as one or more beads. In some embodiments, one or more beads are associated with one or more wells. In some embodiments, the planar surface comprises a biochip or flow cell.

As used herein "array" or "biochip" includes a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

Nucleic acid arrays are known in the art, and can be classified in a number of ways; both ordered arrays (e.g. the ability to resolve chemistries at discrete sites), and random arrays are included. Ordered arrays include, but are not limited to, those made using photolithography techniques (Affymetrix GENECHIP), spotting techniques (Synteni and others), printing techniques (Hewlett Packard and Rosetta), three dimensional "gel pad" arrays, etc. Some embodiments utilize microspheres on a variety of substrates including fiber optic bundles, as are outlined in PCTs US98/21193, PCT US99/14387 and PCT US98/05025; WO98/50782; and U.S. Ser. Nos. 09/287,573, 09/151,877, 09/256,943, 09/316, 154, 60/119,323, 09/315,584; all of which are expressly incorporated herein by reference in their entireties.

As used herein "substrate" can include any insoluble substrate or matrix to which molecules can be attached, such as for example latex beads, dextran beads, polystyrene surfaces, polypropylene surfaces, polyacrylamide gel, gold surfaces, glass surfaces and silicon wafers. The substrate may be a planar glass surface. The substrate may be mounted on the interior of a flow cell to allow the interaction with solutions of various reagents.

As used herein "immobilized" can include direct or indirect attachment to a solid support via covalent or non-covalent bond(s). In some embodiments, covalent attachment may be used, but generally all that is required is that the molecules (for example, nucleic acids) remain immobilized or attached to a support under conditions in which it is intended to use the support, for example in applications requiring nucleic acid amplification and/or sequencing. Typically oligonucleotides to be used as capture oligonucleotides or amplification oligonucleotides are immobilized such that a 3' end is available for enzymatic extension and at least a portion of the sequence is capable of hybridizing to a complementary sequence. Immobilization can occur via hybridization to a surface attached oligonucleotide, in which case the immobilized oligonucleotide or polynucleotide may be in the 3'-5' orientation. Alternatively, immobilization can occur by means other than base-pairing hybridization, such as the covalent attachment. There are a wide variety of known methods of attaching nucleic acids to substrates that include attachment of binding ligands, including nucleic acid probes, to microspheres that are randomly distributed on a surface, including a fiber optic bundle, to form high density arrays. See for example PCTs US98/21193, PCT US99/14387 and PCT US98/05025; WO98/50782; and U.S. Ser. Nos. 09/287,573, 09/151,877, 09/256,943, 09/316,154, 60/119,323, 09/315,584; all of which are expressly incorporated herein by reference in their entireties.

In some embodiments, an array can include one or more different nucleic acids. In some embodiments, an array can include one or more different substrate probes; and/or one or more different capture probes. In some embodiments, an array can include one or more different anchor probes; one or more different extended ligated anchor probes; and/or one or more different extended ligated target nucleic acids. Arrays containing from about 2 different nucleic acids to many millions can be made, with very large arrays being possible. Generally, the array will comprise from two to as many as a billion or more, depending on the size of the beads and the substrate, as well as the end use of the array, thus very high density, high density, moderate density, low density and very low density arrays may be made. Some embodiments include very high density arrays are from about 10,000,000 nucleic acids/cm$^2$ to about 2,000,000,000 nucleic acids/cm$^2$, with from about 100,000,000 nucleic acids/cm$^2$ to about 1,000,000,000 nucleic acids/cm$^2$ being preferred. Some embodiments include high density arrays range about 100,000 nucleic acids/cm$^2$ to about 10,000,000 nucleic acids/cm$^2$, with from about 1,000,000 nucleic acids/cm$^2$ to about 5,000,000 nucleic acids/cm$^2$. Some embodiments include moderate density arrays range from about 10,000 nucleic acids/cm$^2$ to about 100,000 nucleic acids/cm$^2$, and from about 20,000 nucleic acids/cm$^2$ to about 50,000 nucleic acids/cm$^2$. Some embodiments include low density arrays are generally less than 10,000 nucleic acids/cm$^2$, with from about 1,000 nucleic acids/cm$^2$ to about 5,000 nucleic acids/cm$^2$. Some embodiments include very low density arrays are less than 1,000 nucleic acids/cm$^2$, with from about 10 nucleic acids/cm$^2$ to about 1000 nucleic acids/cm$^2$, and from about 100 nucleic acids/cm$^2$ to about 500 nucleic acids/cm$^2$.

In some embodiments, the surface of a substrate is modified to contain wells, for example, depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

As used herein "microspheres" or "beads" or "particles" or grammatical equivalents can include small discrete particles. The composition of the beads will vary, depending on the class of capture probe and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "Microsphere Detection Guide" from Bangs Laboratories, Fishers Ind. is a helpful guide, which is incorporated herein by reference in its entirety. The beads need not be spherical; irregular particles may be used. In addition, the beads may be porous, thus increasing the surface area of the bead available for either capture probe attachment or tag attachment. The bead sizes range from nanometers, for example, 100 nm, to millimeters, for example, 1 mm, with beads from about 0.2 micron to about 200 microns being preferred, and from about 0.5 to about 5 micron being particularly preferred, although in some embodiments smaller beads may be used.

Method of Sequencing Nucleic Acids

Some of the methods and compositions provided herein include methods of sequencing nucleic acids. In some embodiments, a nucleic acid library is prepared using the methods provided herein. A number of DNA sequencing techniques are known in the art, including fluorescence-based sequencing methodologies (See, e.g., Birren et al., Genome Analysis Analyzing DNA, 1, Cold Spring Harbor, N.Y., which is incorporated herein by reference in its entirety). In some embodiments, automated sequencing techniques understood in that art are utilized. In some embodiments, parallel sequencing of partitioned amplicons can be utilized (PCT Publication No WO2006084132, which is incorporated herein by reference in its entirety). In some embodiments, DNA sequencing is achieved by parallel oligonucleotide extension (See, e.g., U.S. Pat. No. 5,750,341; U.S. Pat. No. 6,306,597, which are incorporated herein by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803, which are incorporated by reference), the 454 picotiter pyrosequencing technology (Margulies et al., 2005 Nature 437, 376-380; US 20050130173, which are incorporated herein by reference in their entireties), the Solexa single base addition technology (Bennett et al., 2005, Pharmacogenomics, 6, 373-382; U.S. Pat. No. 6,787,308; U.S. Pat. No.

6,833,246, which are incorporated herein by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330, which are incorporated herein by reference in their entireties), and the Adessi PCR colony technology (Adessi et al. (2000). Nucleic Acid Res. 28, E87; WO 00018957, which are incorporated herein by reference in their entireties).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al, Nature Rev. Microbiol, 7-287-296; which are incorporated herein by reference in their entireties). NGS methods can be broadly divided into those that typically use template amplification and those that do not. Amplification-utilizing methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos Biosciences, SMRT sequencing commercialized by Pacific Biosciences, and emerging platforms marketed by VisiGen and Oxford Nanopore Technologies Ltd.

In pyrosequencing (U.S. Pat. No. 6,210,891; U.S. Pat. No. 6,258,568, which are incorporated herein by reference in their entireties), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and 106 sequence reads can be achieved, resulting in up to 500 million base pairs (Mb) of sequence.

In the Solexa/Illumina platform (Voelkerding et al, Clinical Chem., 55-641-658, 2009; MacLean et al, Nature Rev. Microbiol, 7:287-296; U.S. Pat. No. 6,833,246; U.S. Pat. No. 7,115,400; U.S. Pat. No. 6,969,488, which are incorporated herein by reference in their entireties), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluorophore and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al, Clinical Chem., 55-641-658, 2009; U.S. Pat. No. 5,912,148; U.S. Pat. No. 6,130,073, which are incorporated herein by reference in their entireties) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al., J. Am. Chem. Soc. 2006 Feb. 8; 128(5):1705-10, which is incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore (or as individual nucleotides pass through the nanopore in the case of exonuclease-based techniques), this causes a change in the magnitude of the current through the nanopore that is distinct for each of the four bases, thereby allowing the sequence of the DNA molecule to be determined.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, which are incorporated herein by reference in their entireties). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

Kits and Systems

Some embodiments of the methods and compositions provided herein include kits and systems for preparing nucleic acid libraries. Some such kits and systems can include a flow cell comprising a biochip and one or more reagents. In some embodiments, the biochip comprises a substrate comprising a plurality of substrate probes and a plurality of capture probes immobilized thereon. One or more substrate probes can be different; one or more capture probes can be different. In some embodiments, the substrate probes and capture probes are located at discrete sites on the substrate. In some embodiments, the discrete sites are wells.

In some embodiments, the reagents comprise adapter nucleic acids comprising sequences complementary to a substrate probe and a target nucleic acid. In some embodiments, adapter nucleic acids comprise target nucleic acid sequences and sequences complementary to a capture probe. In some embodiments, the reagents include a recombinase, such as RecA, and an appropriate buffer. In some embodiments, the reagents include a sample comprising a target nucleic acid. In some embodiments, the reagents include a target nucleic acid.

EXAMPLES

Example 1—Biochip Preparation and Target Amplification

FIG. 1 shows an example in which a flow cell comprising a biochip is adapted to capture a certain target nucleic acid, and the captured target nucleic acid is amplified by cluster amplification. A flow cell comprising a biochip is obtained comprising a substrate probe comprising the universal P7 primer and a capture probe comprising the universal P5 primer, each probe is immobilized on the biochip. An adapter nucleic acid is prepared comprising sequences complementary to the P7 primer (P7'), sequencing primer (SBS2'), and an upstream locus specific sequence of a target nucleic acid (USLO'). The adapter nucleic acid is injected into the flow cell, and the adapter nucleic acid hybridizes to the substrate probe. The substrate probe is extended by polymerase extension to form an anchor probe that can selectively bind to a target nucleic acid. The adapter nucleic acid and extended substrate probe are denatured, and the biochip washed to remove the adapter nucleic acid.

A ligation probe is obtained comprising sequences complementary to the P5 primer (P5'), sequencing primer (SBS1'), and a downstream locus specific sequence of a target nucleic acid (DSLO'). The ligation probe, sample nucleic acid comprising the target nucleic acid, and RecA recombinase is injected into the flow cell. The DSLO' portion of the ligation probe and the USLO' portion of the anchor probe each selectively hybridize to corresponding portions of the target nucleic acid under conditions in which the RecA promotes the hybridization.

The hybridized anchor probe is extended by polymerase extension with a sequence complementary to the target nucleic acid sequence, and the extended anchor probe is ligated to the hybridized ligation probe. The target nucleic acid and extended ligated anchor probe are denatured, the biochip washed, and the target nucleic acid removed. The portion of the extended ligated anchor probe comprising the P5' sequence is hybridized to the capture probe, and the capture probe extended. The complex is amplified by cluster amplification.

Example 2—RecA-Based Library Preparation

In this example, nucleic acid libraries were prepared using either RecA or thermal denaturation (TD) to promote hybridization of target nucleic acids and target-specific probes. For RecA promoted hybridization assays: an oligo probe pool comprising primers complementary to the target nucleic acid upstream and downstream of the region of interest and D-loop reaction buffer (2 μM RecA or 10 μM RecA, 0.1 mM ATPγS, 50 mM NaOAc, 1 mM TCEP, 10 mM DTT, and 0.1 mg/mL BSA) were mixed and incubated for 5 minutes at 37° C. to promote a filament reaction. Target DNA was added to the filament reaction and incubated for 10 minutes at 37° C. to promote strand invasion. For thermal denaturation promoted hybridization assays: target nucleic acid and oligo probe pool were denatured by heating, and annealing. The amounts of the target DNA and the oligo probe pool were the same in each assay.

Figure 2:
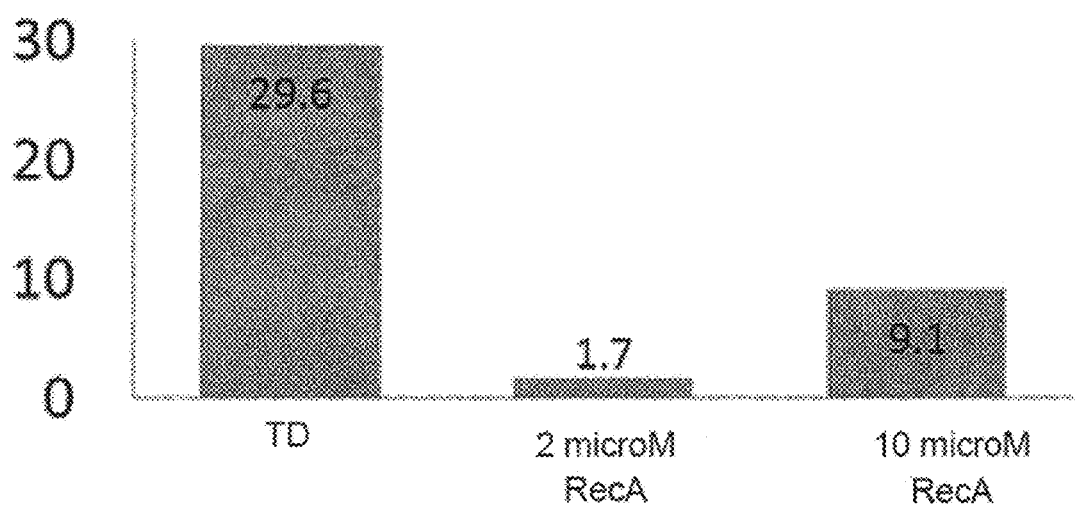
FIG. 2 depicts a graph for the amount of nucleic acid produced in assays in which hybridization of probes to double-stranded nucleic acids was promoted by thermal denaturation, or the recombinase, RecA.

Each reaction mixture was transferred to a filter plate and processed identical to a standard protocol. Briefly, a first hybridized probe was extended and ligated to a second hybridized probe. The extended ligated product was amplified using amplification primers comprising indices and universal primers, P5 or P7. The recovered products were gel analyzed and purified. The purified product concentrations are reported in FIG. 2. Table 1 shows quality control results using the purified products in sequencing reactions.

TABLE 1

| Parameter | QC specifications | Thermal Denaturation | RecA-denaturation (2 μM RecA) | RecA-denaturation (10 μM RecA) |
| --- | --- | --- | --- | --- |
| Mean depth |  | 4982 | 1493 | 2932 |
| % specificity | 63 | 71 | 63 | 50 |
| % uniformity | 80 | 96 | 76 | 88 |
| Amplicon dropout % | 2.5 | 0 | 2.6 | 0 |

Figure 3:
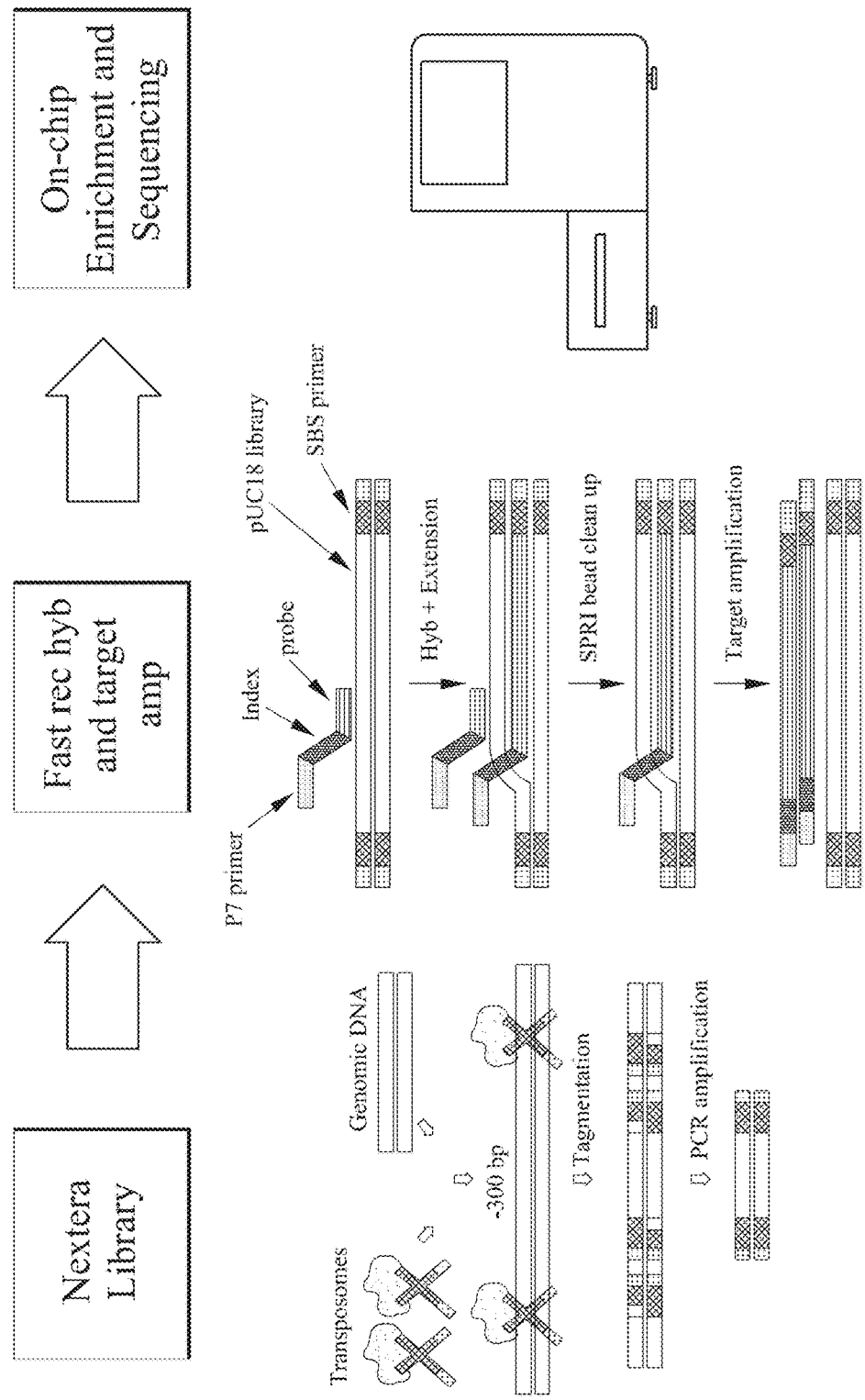
FIG. 3 depicts an embodiment of a work flow for obtaining a targeted nucleic acid library in which a nucleic acid library is obtained, a double-stranded nucleic acid is hybridized to a probe comprising a P7 primer under conditions in which a recombinase promotes the hybridization and a polymerase extends the probe.

Example 3—Targeted Library Preparation and On-Chip Target Capture and Enrichment This example demonstrates fast recombinase-based hybridization of a probe with a target nucleic acid in a nucleic acid library. Briefly, a NEXTERA nucleic acid library was prepared. The double-stranded target nucleic acid was hybridized with a target-specific adapter probe comprising target-specific sequences, an index, and a P7 primer under conditions in which a recombinase promotes the hybridization. The hybridized probe was extended, and optionally amplified. FIG. 3 summarizes the work flow. First, a pUC18 Nextera library was prepared using mosaic ends (MEs). The tagmented products were amplified with the indexed ME primers. The P5 and P7 adapters were omitted. Next, adapter probes that contain the P7 complement and an index were hybridized to the target using a recombinase (UvsX). Furthermore, the recombinase solution contained a polymerase and nucleotides to trigger extension post hybridization. The newly synthesized P7 target strand (extended adapter probe) contained a P7 primer complement, target nucleic acid complement, and indexed ME. A SPRI bead clean up protocol was used to separate unreacted P7 probes from the extended P7 adapter probes. Then, optionally, P7 and index ME primers were used to selectively amplify the newly synthesized P7 target strand. These products, either with or without the optional amplification, were introduced into a flow cell, for target capture and enrichment prior to sequencing.

Figure 4:
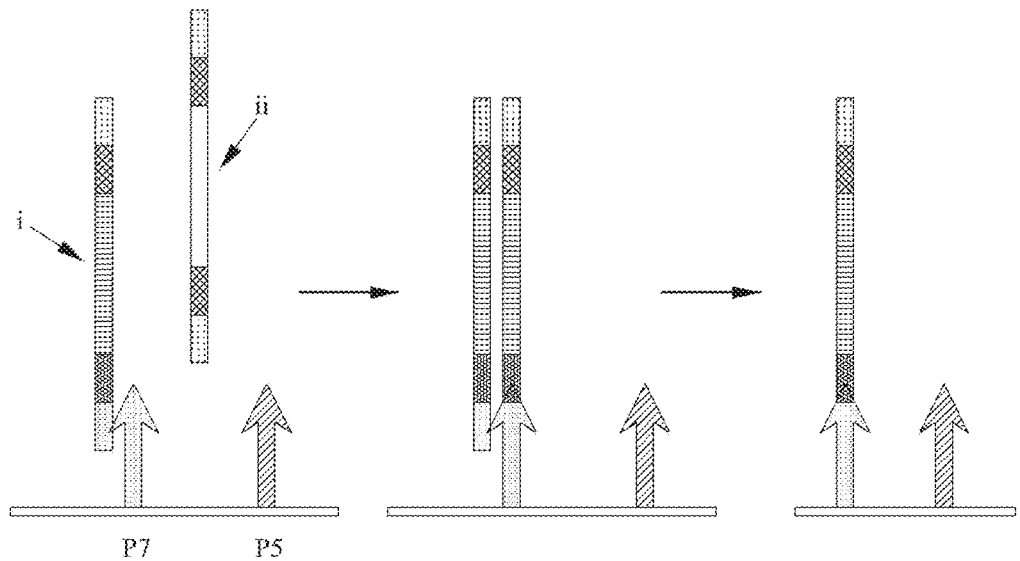
FIG. 4 depicts an embodiment of a method for enriching a nucleic acid on a biochip by extending a substrate probe by a first polymerase extension, and further extending the substrate probe by a second polymerase extension to prepare a substrate for cluster amplification on the biochip.
Figure 4:
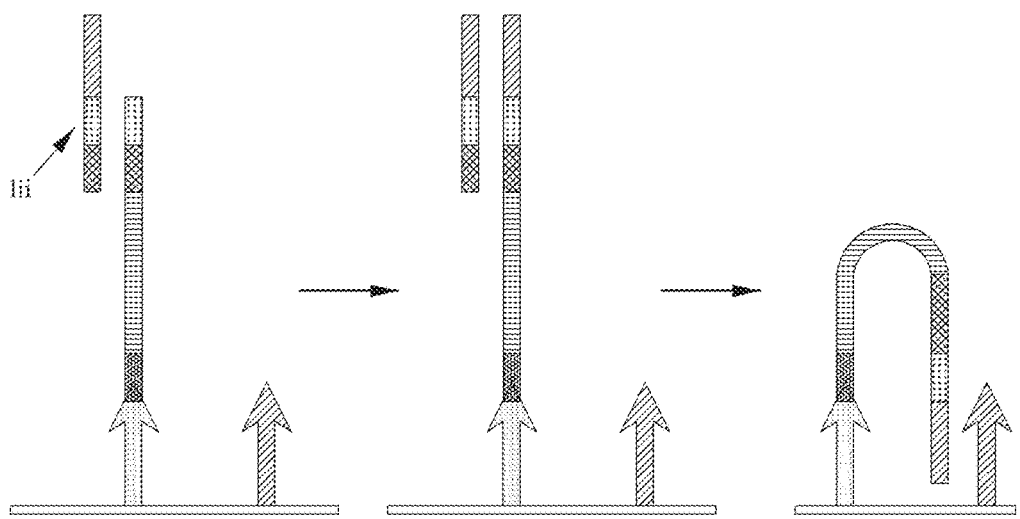

Standard MiSeq flow cells (Illumina. Inc., San Diego) were used to demonstrate a method for on-chip target capture and enrichment using the product of the method described in FIG. 3. FIG. 4 summarizes the method. The flow cells each comprised a biochip with surface-attached substrate probes, comprising the universal P7 primer and surface-attached capture probe comprising the universal P5 primer. The product of the procedure described in FIG. 3, the P7 target strand (comprising sequences complementary to the P7 primer (P7') and a target nucleic acid), as well as the NEXTERA library, was injected into the flow cell. Only P7 target strand hybridized to the substrate probe. (FIG. 4, panel 1). The substrate probe was extended by polymerase extension to provide a substrate probe comprising the target sequence (FIG. 4, panel 2). The P7 target strand and extended substrate probe were denatured, and the biochip washed to remove the P7 target strand (FIG. 4, panel 3). An adapter nucleic acid comprising P5 capture probe sequences and sequences complementary to the extended substrate probe was hybridized to the extended substrate probe (FIG. 4, panel 4). The extended substrate probe was further extended by polymerase extension with sequences complementary to the adapter nucleic acid, including the P5 capture probe (FIG. 4, panel 5). The adapter nucleic acid and further extended substrate probe were denatured, and the biochip washed to remove the adapter nucleic acid. The further extended substrate probe was hybridized to the capture probe, and cluster amplification was carried out (FIG. 4, panel 6). Table 2 shows MiSeq reporter enrichment results; read enrichment was 99.1%.

TABLE 2

| Sample ID: | 0816pcr |
|---|---|
| Runfolder: | A4W08 |
| Padding size: | 150 |
| Total length of targeted reference: | 401 |
| Total aligned reads: | 552601 |
| Targeted aligned reads: | 547619 |
| Read enrichment: | 99.10% |
| Padded target aligned reads: | 547991 |
| Padded read enrichment: | 99.20% |
| Total aligned bases: | 19748476 |
| Targeted aligned bases: | 19567408 |
| Base enrichment: | 99.10% |
| Padded target aligned bases: | 19582974 |
| Padded base enrichment: | 99.00% |
| Percent duplicate paired reads: | 0.00% |
| Mean region coverage depth: | 48796.5 |
| Uniformity of coverage (Pct > 0.2*mean): | 30.70% |
| Target coverage at 1X: | 100.00% |
| Target coverage at 10X: | 100.00% |
| Target coverage at 20X: | 100.00% |
| Target coverage at 50X: | 94.50% |

Figure 5:
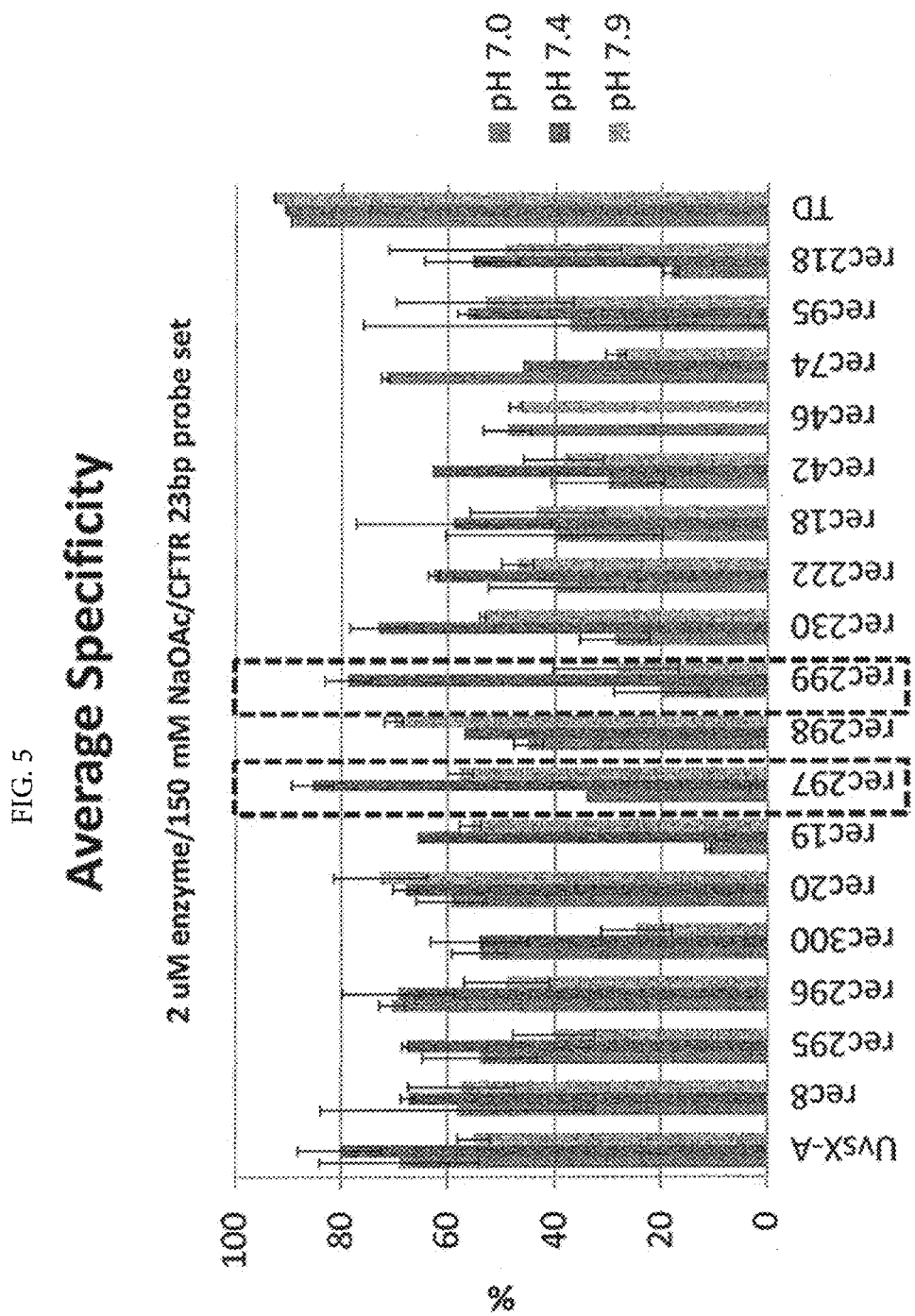
FIG. 5 is a graph of the average percentage specificity for various recombinases in hybridization assays. Probes hybridized to target nucleic acids under conditions promoted by a recombinase. Controls include hybridization using thermal denaturation (TD) alone.

Example 4—Screening Recombinases for Use in Preparing Targeted Nucleic Acid Libraries This example demonstrates the use of certain recombinases in hybridization assays in which probes were hybridized to target nucleic acids. Controls included hybridization in the absence of a recombinase, using thermal denaturation (TD) only. Eighteen engineered recombinases were screened. FIG. 5 shows a graph of the average specificity for screened recombinases. The recombinases Rec297, rec299 and UvsX recombinases had the highest specificity at pH 7.4, with specificities similar to those obtained in assays in the absence of a recombinase, using thermal denaturation (TD) only.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for preparing a substrate-bound anchor probe comprising a sequence of a target nucleic acid comprising:
    (a) providing a nucleic acid library comprising a plurality of different nucleic acids, wherein the nucleic acid library comprises a double-stranded target nucleic acid;
    (b) hybridizing a first adapter probe with the target nucleic acid in the presence of a recombinase,
        wherein the first adapter probe comprises a first portion complementary to a substrate probe and a second portion complementary to at least a portion of the double-stranded target nucleic acid, and
        wherein the recombinase promotes hybridizing the second portion with the double-stranded target nucleic acid;
    (c) extending the hybridized first adapter probe;
    (d) hybridizing the extended adapter probe with the substrate probe, wherein the substrate probe is immobilized on a first substrate; and
    (e) extending the hybridized substrate probe to form a substrate-bound anchor probe comprising the sequence of the target nucleic acid.

2. The method of claim 1, further comprising amplifying the substrate-bound anchor probe, the amplifying comprising:
(f) hybridizing a second adapter probe with the substrate-bound anchor probe, wherein the second adapter probe comprises a first portion complementary to a capture probe and a second portion complementary to at least a portion of the substrate-bound anchor probe;
(g) extending the hybridized, substrate-bound anchor probe to form an extended anchor probe;
(h) hybridizing the extended anchor probe with the capture probe, wherein the capture probe is immobilized on a second substrate; and
(i) extending the capture probe to form an immobilized, modified capture probe.

3. The method of claim 1, wherein (c) comprises polymerase extension.

4. The method of claim 3, wherein the polymerase extension comprises a polymerase chain reaction.

5. The method of claim 1, wherein (e) comprises polymerase extension.

6. The method of claim 1, wherein (e) comprises ligation of a nucleic acid complementary to the extended adapter probe with the substrate probe.

7. The method of claim 1, wherein the first adapter probe comprises a sequence selected from the group consisting of a locus-specific sequence and an allele-specific sequence.

8. The method of claim 2, wherein the second adapter probe comprises a sequence selected from the group consisting of a locus-specific sequence and an allele-specific sequence.

9. The method of claim 1, wherein the double-stranded target nucleic acid comprises genomic DNA.

10. The method of claim 1, wherein the recombinase is RecA.

11. The method of claim 1, wherein the first substrate comprises a bead.

12. The method of claim 11, wherein the bead is associated with an individual site of a substrate.

13. The method of claim 12, wherein the site is configured to have a single associated bead.

14. The method of claim 2, wherein the first and the second substrate are the same substrate.

15. The method of claim 1, wherein the nucleic acids in the starting nucleic acid library comprise one or more sequences selected from mosaic elements, indices, and sequencing adapters.

16. The method of claim 1, wherein the nucleic acid library is produced by tagging and fragmenting activities of a transposase.

17. A method of detecting a plurality of nucleic acid sequences comprising: obtaining a plurality of immobilized, modified capture probes prepared according to claim 2; and detecting the immobilized, modified capture probes, thereby detecting the plurality of target nucleic acid sequences.

18. A method of preparing a nucleic acid library comprising:
(a) providing a plurality of anchor probes, wherein the anchor probes are each immobilized on a substrate;
(b) hybridizing a plurality of double-stranded target nucleic acids with the plurality of anchor probes in the presence of a recombinase under conditions wherein the recombinase promotes the hybridizing with the target nucleic acids;
(c) hybridizing the plurality of double-stranded target nucleic acids with a plurality of ligation probes in the presence of a recombinase under conditions wherein the recombinase promotes the hybridizing with the target nucleic acids;
(d) extending the anchor probes or the ligation probes; and
(e) ligating the anchor probes to the ligation probes to form a plurality of different extended ligated probes, wherein the extended ligated probes are immobilized to the substrate, thereby preparing the library of nucleic acids.

19. A method of detecting a nucleic acid comprising:
(a) providing an anchor probe, wherein the anchor probe is immobilized on a substrate;
(b) hybridizing a double-stranded target nucleic acid with the anchor probe in the presence of a recombinase under conditions wherein the recombinase promotes the hybridizing with the target nucleic acid;
(c) hybridizing the double-stranded target nucleic acid with a ligation probe in the presence of a recombinase under conditions wherein the recombinase promotes the hybridizing with the target nucleic acid;
(d) extending the anchor probe or the ligation probe;
(e) ligating the anchor probe to the ligation probe to form an extended ligated probe, wherein the extended ligation probe is immobilized to the substrate; and
(f) detecting the extended ligated probe, thereby detecting the nucleic acid.

20. The method of claim 18, wherein the substrate is a flow cell.

21. The method of claim 18, wherein the anchor probe and the extended ligated probe are covalently immobilized to the substrate.

22. The method of claim 18, further comprising amplifying the extended ligated probes by cluster amplification.

23. The method of claim 19, wherein the detecting is by next-generation sequencing.

* * * * *